United States Patent [19]

Szwarc

[11] Patent Number: 4,964,866

[45] Date of Patent: Oct. 23, 1990

[54] NEEDLE SHEATH ASSEMBLY

[75] Inventor: Joseph M. Szwarc, Cedar Grove, N.J.

[73] Assignee: Becton, Dickinson and Company, Franklin Lakes, N.J.

[21] Appl. No.: 440,915

[22] Filed: Nov. 22, 1989

[51] Int. Cl.$^5$ ............................................. A61M 5/32
[52] U.S. Cl. .................................... 604/192; 604/263
[58] Field of Search ............... 604/192, 197, 199, 263; 206/364

[56] References Cited

U.S. PATENT DOCUMENTS

| | | | |
|---|---|---|---|
| 2,671,450 | 3/1954 | Dann | 604/192 |
| 2,688,963 | 9/1954 | Smith | 604/192 |
| 2,831,483 | 4/1958 | Lorenzo | 604/192 |
| 3,865,236 | 2/1975 | Rycroft | 206/364 |
| 4,317,446 | 3/1982 | Ambrosio et al. | 604/193 |
| 4,334,536 | 6/1982 | Pfleger | 604/263 |
| 4,430,082 | 2/1984 | Schwabacher | 604/263 |
| 4,636,201 | 1/1987 | Ambrose et al. | 604/192 |
| 4,742,910 | 5/1988 | Staebler | 604/192 |

Primary Examiner—C. Fred Rosenbaum
Assistant Examiner—Sharon Rose
Attorney, Agent, or Firm—John L. Voellmicke

[57] ABSTRACT

A hypodermic syringe assembly includes a barrel having an open proximal end, a chamber for retaining fluid and a tip portion extending from a distal end of the barrel having a passageway therethrough communicating with the chamber. A needle cannula having a distal end extends outwardly from the tip portion and includes a lumen in fluid communication with the passageway. A needle shield assembly includes a resilient needle sheath having an open proximal end, a closed distal end, a sidewall defining a receptacle therein and is positioned within an elongate rigid shield having an open proximal end, a distal end and a sidewall therebetween. Structure for holding the sheath within the shield is provided so that the sheath cannot be removed from the shield during normal use of the syringe assembly. The sheath includes cannula sealing means at the distal end of the receptacle. The needle shield assembly is positioned with the distal end of the cannula engaging the cannula sealing means and the proximal end of the sheath removably engaging the tip portion to hold the needle shield assembly on the barrel while simultaneously sealing the lumen of the cannula so that the sheath surrounds the entire portion of the cannula which extends outwardly from the tip portion of the barrel.

27 Claims, 4 Drawing Sheets

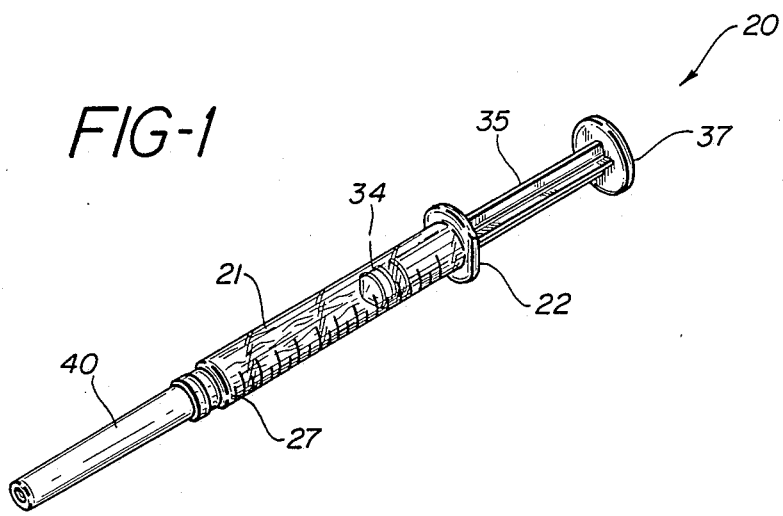
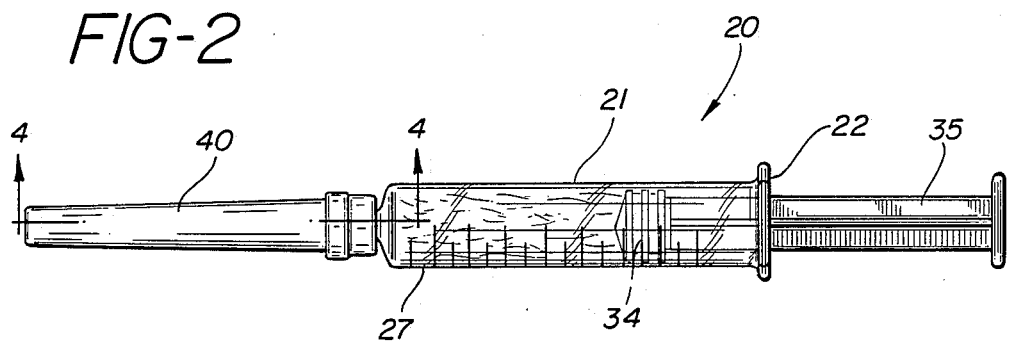
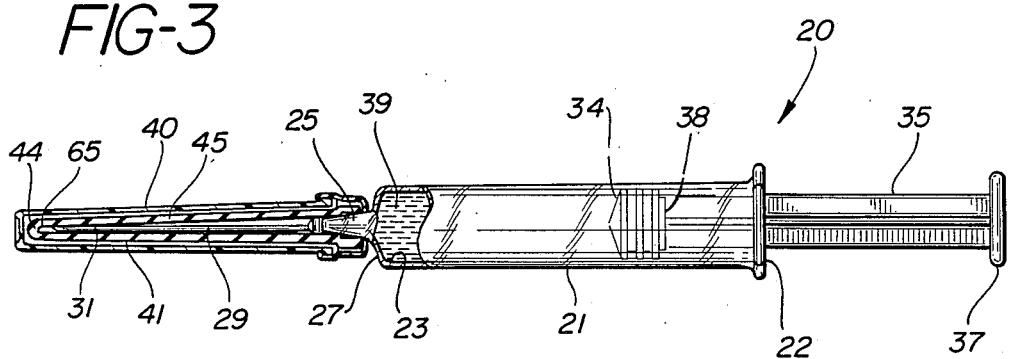

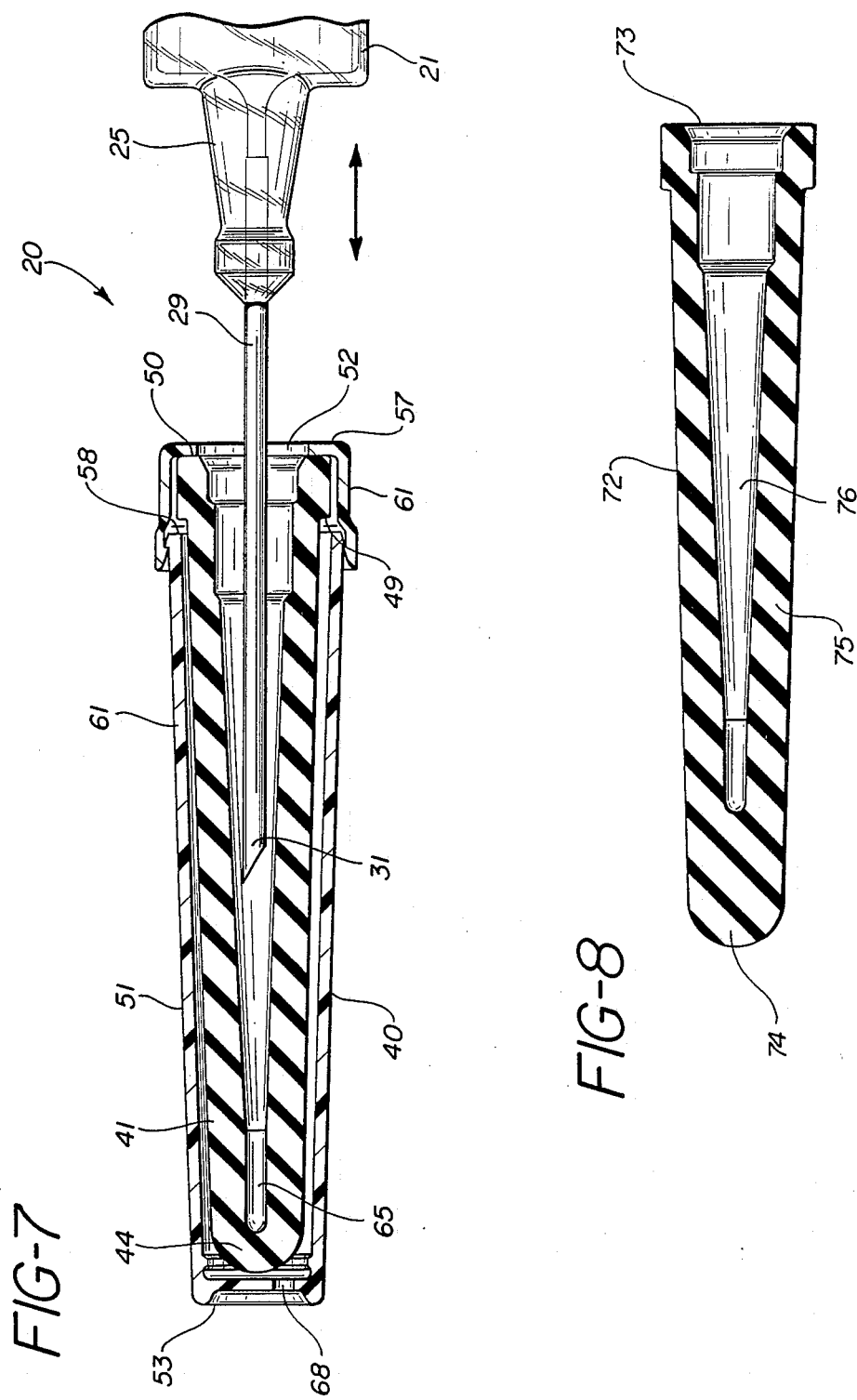

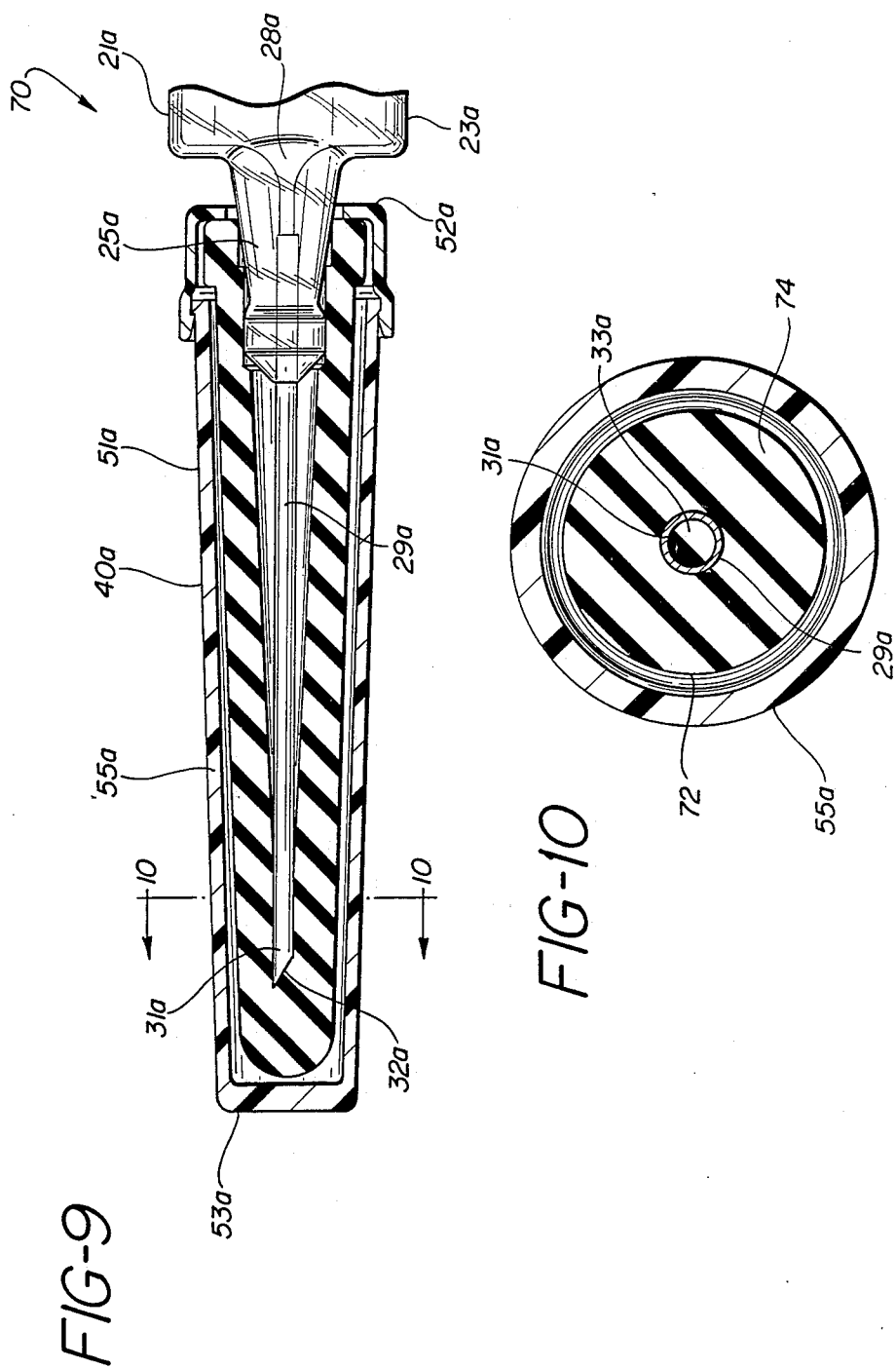

NEEDLE SHEATH ASSEMBLY

BACKGROUND OF THE INVENTION

1. Field of the Invention

The present invention relates to a hypodermic syringe assembly, and more particularly concerns a hypodermic syringe suitable for prefilling including a needle shield assembly having cannula sealing features and features to help prevent accidental needle sticks.

2. Description of the Prior Art

Many injectable medications are packaged and distributed in the hypodermic syringe that will eventually be used to administer the medication to the patient. Prefilled syringes are available from pharmaceutical manufacturers, and syringes are frequently prefilled in hospital pharmacies. In both instances, the prefilled syringe is subject to a variety of environmental challenges during storage, shipping and/or handling before the medication is administered to the patient. Accordingly, the contents of the syringe must be sealed to preserve their sterility.

Articles such as hypodermic syringe tip caps are sometimes used to seal the distal tip of a prefilled hypodermic syringe. Syringes having a permanently attached needle cannula can be sealed with a resilient needle shield as taught in U.S. Pat. No. 3,865,236 to Rycroft. Rycroft teaches a needle shield of resilient rubber closed at one end and adapted to be positioned in surrounding relationship with respect to the needle so as to normally maintain the needle in a sealed atmosphere. The needle shield of Rycroft seals the cannula so that the prefilled medication is not in fluid communication with the environment.

Resilient rubber needle shields such as those taught by Rycroft are widely used and accepted. However, in recent years there has developed an increased concern regarding the transfer of disease and/or infection to syringe users and healthcare professionals who accidentally stick themselves with hypodermic needles while preparing, using or disposing of a hypodermic syringe products. Placing an excessive force on the tip of a syringe and needle assembly having a resilient rubber needle shield may cause the needle to penetrate the needle shield to expose the sharp injection point. Although reshielding is neither preferred nor recommended by many people, circumstances arise where it is necessary or convenient for the user to reshield the needle after injection. A resilient needle shield can present a potential problem if it is reshielded improperly so that the needle pierces the sidewall of the needle shield or the distal end of the needle shield and sticks the user. Syringe assemblies having rigid plastic needle shields avoid some of these problems but are generally not suitable for prefilled glass syringes because they do not have the ability to seal the needle cannula and because of their hardness and relative inelasticity may not effectively attach to the tip of a glass syringe barrel which in normal manufacturing has a much broader range of tolerances than a plastic syringe.

One way to retain the positive and desirable features of the resilient needle shield and to reduce the potential for accidental needle sticks is to provide a hard plastic protector or cover which can be installed over the needle assembly having a barrel with fixed needle cannula and a resilient needle shield in place such as an already prefilled hypodermic syringe assembly. U.S. Pat. No. 4,430,082 to Schwabacher teaches an inflexible hollow cylindrical sleeve which fits over an elastomeric protective needle cover. The cylindrical sleeve is provided with flexible gripping means which when depressed exerts pressure on the inner elastomeric protective cover thereby allowing the cover to be removed along with the protective cylindrical sleeve. Although the teachings of Schwabacher provide an improvement the device still has several shortcomings with respect to prevention of accidental needle stick. First, if the syringe is assembled by hand, there is still the potential of sticking during the assembly process before the rigid cover is applied. After the rigid cover is applied to the syringe assembly it can be removed leaving the needle covered only by the elastomeric protecting cover, effectively returning the device to its original state, before the rigid sleeve was installed, having all the shortcomings recited for syringe assemblies without rigid needle sleeves.

A similar device is taught by Ambrosio et al. in U.S. Pat. No. 4,317,446. Ambrosio et al. teach a plunger rod/protector which fits over a elastomeric needle sheath on a prefilled syringe having a fixed needle cannula. The plunger rod/protector of Ambrosio et al. does not engage the sheath and maintains its position on the syringe assembly by engaging the outer surface of the syringe barrel so that the plunger rod protector can be installed and removed from the distal end of the syringe without removing the elastomeric needle sheath. Ambrosio et al. has all of the disadvantages of Schwabacher in that the initial assembly may still be accomplished manually providing the opportunity for an accidental needle stick and the plunger rod protector may be removed leaving the needle covered only by the elastomeric needle sheath.

A further improvement is taught by Ambrose et al. in U.S. Pat. No. 4,636,201. Ambrose et al. teach a rigid sheath cover adapted to be placed over a rubber needle cover on a hypodermic syringe. The rigid sheath cover has a plurality of spaced cantilever like teeth projecting outwardly from the tubular body of the cover to form the open end. At least two of the teeth include a lip projecting inwardly toward the center of the opening formed by the teeth for ripping the needle cover after installation. Ambrose et al. still have an initial shortcoming in that the syringe having the rubber needle cover is already assembled. Manual assembly or use before installation of the rigid sheath cover provides all of the opportunity for accidental needle sticks as the original prior art syringe before rigid covers are installed. Also, because the rigid sheath is installed over the rubber needle cover there is an opportunity for the user to be stuck by the needle during the process of applying the rigid sheath to the needle assembly of Abrose et al. The rigid sheath cover of Ambrose et al. also provides an additional chance for accidental needle sticks because a needle can properly enter the open end of the rubber needle cover, at an angle, and pass through the cover and the space between the spaced teeth to stick the user. The only apparent advantage of Abrose et al. over the devices of Ambrosio et al. and Schwabacher is that after installation it appears that the rubber needle cover will remain within the rigid sheath. However, the spaced teeth of the Ambrose et al. sheath cover must be flexible enough to deform while passing over a soft rubber needle cover to the final assembled position. If the teeth are very rigid they may not flex enough to pass over the rubber needle cover or tear the cover in the process of assembly. Accordingly, the Ambrose et al. device must perform a balancing act between being flexible enough for proper installation yet strong enough to retain the rubber needle cover after assembly.

Shields for sealing the contents of a prefilled hypodermic syringe and protecting the needle from the environment have been addressed by the prior art. Improvements involving rigid covers and protectors which can be installed on a prefilled syringe having a resilient needle sheath have also been addressed by the prior art. However, there is still a need for a simple, straight forward, reliable, easily fabricated hypodermic syringe assembly having a needle shield assembly which retains the cannula sealing and cleanliness protecting features of the resilient needle sheath and incorporates a rigid shield to help prevent accidental needle sticks during all phases of the assembly and operation and disposal of the syringe.

SUMMARY OF THE INVENTION

The hypodermic syringe assembly of the present invention comprises a barrel having an open proximal end, a chamber for retaining fluid and a tip portion extending from a distal end of the barrel having a passageway therethrough communicating with the chamber. A needle cannula having a distal end extending outwardly from the tip portion of the barrel includes a lumen therethrough in fluid communication with the passageway. A needle shield assembly including a resilient needle sheath having an open proximal end, a closed distal end and a sidewall defining a receptacle therein is positioned within an elongate rigid needle shield having an open proximal end, a distal end and a sidewall therebetween. Structure for holding the sheath within the shield is provided so that the sheath cannot be removed from the shield during normal use of the syringe assembly. The sheath includes cannula sealing means at the distal end of its receptacle. The needle shield assembly is positioned with the distal end of the cannula engaging the cannula sealing means and the proximal end of the sheath removably engaging the tip portion of the barrel to hold the needle shield assembly on the barrel while simultaneously sealing the lumen of the cannula so that the sheath surrounds the entire portion of the cannula which extends outwardly from the tip portion of the barrel.

In accordance with another embodiment of the present invention, a hypodermic syringe assembly comprises an elongate barrel having an open proximal end, a chamber for retaining fluid and a tip portion extending from a distal end of the barrel having a passageway therethrough communicating with the chamber. A needle cannula having a distal end extending outwardly from the tip portion includes a lumen therethrough in fluid communication with the passageway. A needle shield assembly including a resilient needle sheath having an open proximal end, a closed distal end, a sidewall defining a receptacle therein and a projection extending outwardly from its proximal end is positioned within an elongate rigid shield having an open proximal end, a closed distal end and a sidewall therebetween. Means for holding the resilient sheath within the shield is provided so that the sheath cannot be removed from the shield during normal use of the syringe assembly. The holding means includes a first inwardly projecting ledge, in said shield, positioned distally of said sheath projection and a second inwardly projecting ledge, in said shield, positioned distally of said sheath projection. The sheath including cannula sealing means at the distal end of the receptacle for providing a fluid-tight seal between the lumen and the environment of the syringe assembly including an elongate retention conduit having a sidewall adapted to accept the distal end of the cannula in fluid-tight engagement between the outside of the cannula and the conduit sidewall. The needle shield assembly is positioned with the distal end of the cannula engaging the cannula sealing means and the proximal end of the sheath removably engaging the tip portion of the barrel to hold the needle shield assembly on the barrel while simultaneously sealing the lumen of the cannula so that the sheath surrounds the entire portion of the cannula extending outwardly from the tip portion of the barrel. The shield and the sheath are constructed so that the shield cannot be manually assembled or manually separated from the sheath while the sheath is properly positioned sealing the cannula and engaging the tip portion of the barrel. The needle shield assembly is easily engageable and removable from the barrel and the cannula using manual force. A stopper is slidably positioned in fluid-tight engagement inside the barrel and is adapted to engage a plunger rod to facilitate its operation. The stopper is capable of moving fluid from the chamber through the passageway upon its movement toward the distal end of the barrel. The stopper is capable of facilitating the drawing of fluid into the chamber through the passageway upon its movement away for the distal end of the barrel. Medicament is included within the chamber between the stopper and the distal end of the barrel. An alternative embodiment of the present invention includes a needle shield assembly for use with the syringe barrel having a chamber for retaining fluid, a tip portion extending outwardly from a distal end of a barrel having a passageway therethrough, and a needle having a distal end extending outwardly form the tip portion having a lumen therethrough in fluid communication with the passageway. The needle shield assembly comprises a resilient needle sheath having an open proximal end, a closed distal end, a sidewall defining a receptacle therein and a projection extending outwardly from said proximal end. The resilient needle sheath is positioned within an elongate rigid shield having an open proximal end, a closed distal end and a sidewall therebetween. Means for holding the sheath within the shield so that the sheath cannot be removed from the shield during normal use of the syringe assembly includes a first inwardly projecting ledge, in the shield, positioned proximally of the sheath projection and a second inwardly projecting ledge in the shield, positioned distally of the sheath projection. The sheath includes needle cannula sealing means at the distal end of the receptacle for providing a fluid-tight seal between the lumen and the environment of the assembly. The needle shield assembly is sized so that the distal end of the cannula is adapted to engage the cannula sealing means and the proximal end of the sheath is adapted to engage the tip portion to hold the syringe assembly on the barrel while simultaneously sealing the lumen of the cannula so that the sheath may surround the entire portion of the cannula which extends outwardly from the tip portion. The shield and the sheath are structured so that the shield cannot be manually assembled or manually separated from the sheath while the sheath is properly positioned sealing the cannula and engaging the tip portion of the barrel.

In accordance with the principles of the present invention, a number of advantages and objectives are attained. Primarily, the present invention provides a simple, straight forward, reliable, easily fabricated syringe having a needle shield assembly which retains the cannula sealing and cleanliness protecting features of the resilient needle sheath, and incorporates a rigid shield to help prevent accidental needle sticks during all phases of the assembly and operation and disposal of the syringe.

BRIEF DESCRIPTION OF THE DRAWINGS

FIG. 1 is a perspective view of the preferred embodiment of the hypodermic syringe assembly of the present invention;

FIG. 2 is a side elevation view of the syringe assembly of FIG. 1;

FIG. 3 is a partial cross sectional view of the syringe assembly of FIG. 1;

FIG. 7 is the syringe assembly of FIG. 4 illustrating the needle shield assembly being partially removed from the syringe barrel and needle assembly;

FIG. 8 is an alternative embodiment of the resilient needle sheath of the present invention;

FIG. 9 is a partial cross sectional view of the syringe assembly of the present invention illustrating the alternative resilient needle sheath; and FIG. 10 is an enlarged cross sectional view of the syringe assembly of FIG. 9 taken along line 10—10.

DETAILED DESCRIPTION

Figure 4:
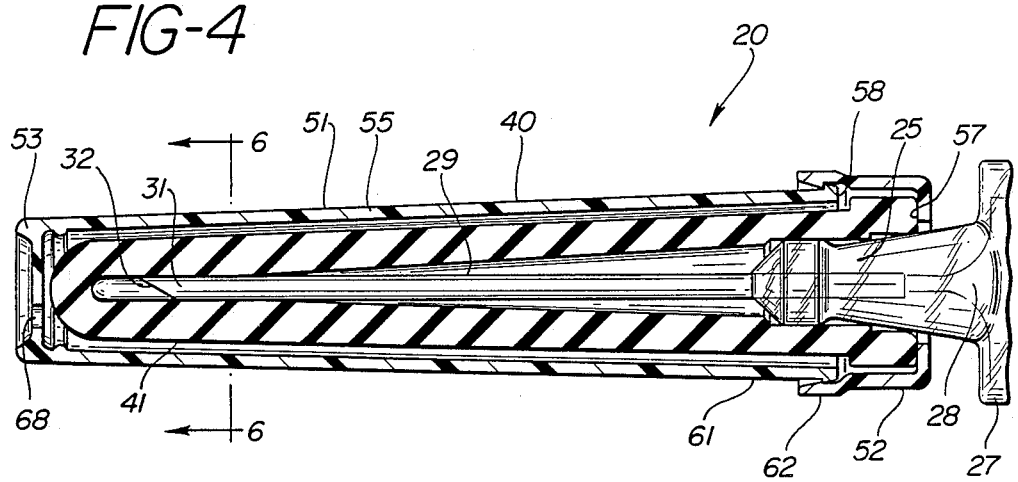
FIG. 4 is an enlarged partial cross-sectional view of the syringe assembly of FIG. 2 taken along line 4—4.
Figure 5:
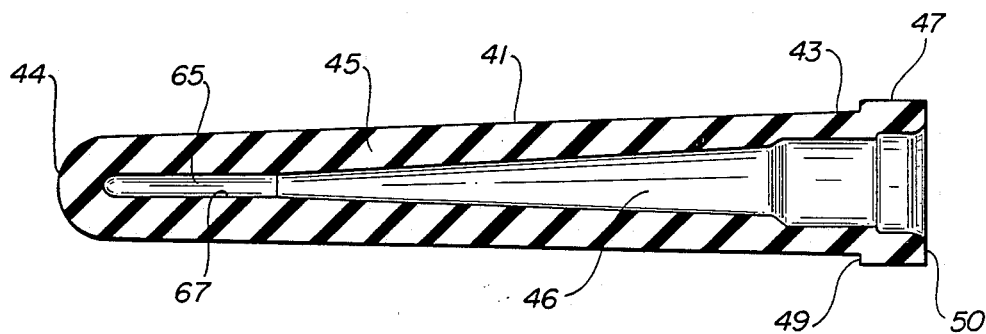
FIG. 5 is a cross sectional view of the resilient needle sheath of the needle shield assembly of the syringe of FIG. 1.

While this invention is satisfied by embodiments in many different forms, there are shown in the drawings and will herein be described in detail preferred embodiments of the invention with the understanding that the present disclosure is to be considered exemplary of the principles of the invention and is not intended to limit the scope of the invention to the embodiments illustrated. The scope of the invention will be measured by the appended claims and their equivalents.

Adverting to FIGS. 1–7, a preferred hypodermic syringe assembly 20 includes an elongate substantially cylindrical syringe barrel 21 having an open proximal end 22, a chamber 23 for retaining fluid and a tip portion 25 extending from a distal end 27 of the barrel having a passageway 28 therethrough communicating with the chamber.

For the purposes of the description of the present invention, the term "distal end" is meant to refer to the end furthest from the person holding the syringe, whereas the term "proximal end" is meant to refer to the end closest to the holder of the syringe.

Needle cannula 29 having a distal end 31 including a sharpened point 32 extends outwardly from tip portion 25. Needle cannula 29 includes a lumen 33 therethrough in fluid communication with passageway 28.

A stopper 34 is slidably in fluid-tight engagement inside the barrel and is adapted to engage a plunger rod 35 to facilitate its operation. In this embodiment, the stopper contains an internal thread (not shown) which engages an external thread not shown) on the plunger rod. The plunger rod is accessible outside of the proximal end of the barrel and is provided to move the stopper along the barrel to force fluid into and out of the chamber through the passageway. Specifically, the stopper is capable of moving fluid from chamber 23 through the passageway upon its movement toward the distal end 27 of the barrel. The stopper is capable of facilitating the drawing of fluid into the chamber through the passageway upon its movement away from the distal end. Disc-shaped plunger rod flange 37 is provided as a convenient structure for applying forces to move the plunger rod with respect to the barrel. A stopper flange 38 on the plunger rod is provided to supply a large surface area to transmit force from the plunger rod to the stopper in a direction toward the stopper, without damaging the stopper. The plunger rod may be installed when the syringe is assembled, or may be provided as a separate unattached component which is engaged to the stopper at the time of use. It will be apparent to one skilled in the art that numerous constructions can be used to join a stopper and a plunger rod and that the arrangement described above is exemplary of these many possibilities. Also, it is within the purview of this invention to include a one piece plunger rod stopper assembly.

A medicament such as liquid medication 39 is contained within the chamber between the stopper and the distal end of the barrel. Medicaments such as solid or powder medication may be contained in the chamber. When solid or powdered medications are used, a diluent must be drawn into the chamber to mix with the medication before injection.

An important feature of the instant invention, representing a substantial improvement over the prior art, is needle shield assembly 40 which includes a resilient needle sheath 41 having an open proximal end 43, a closed distal end 44, a sidewall 45 defining a receptacle 46 therein. The needle sheath also includes a projection extending outwardly from proximal end 43. In this preferred embodiment the projection is an annular flange 47 positioned at the proximal end of the sheath. The resilient needle sheath is positioned within an elongate rigid shield 51 having a continuous open proximal end 52, a distal end 53 and a sidewall 55 therebetween.

A shortcoming of prior art devices is that the very resilient needle cover can be placed over the barrel and needle assembly before the rigid cover is applied and/or the rigid cover may be removed from the resilient needle cover after assembly. When a resilient needle cover is being installed on a needle and barrel assembly, without a rigid cover there exists the potential danger of accidental needle sticks. Also, when the needle and barrel assembly having a resilient cover installed, without the rigid cover, is being handled or used there exists the potential danger of accidental needle sticks. The presence of a rigid cover at these times would further reduce this potential danger. It should be noted that without rigid cover the needle with flexible cover can be bent or damaged by external forces applied to the flexible cover. A bent needle is believed to be a potential danger because the sharp needle point is not directed along the axis of the barrel as the user assumes it is.

It is an object of this invention to provide a needle shield assembly having a resilient sheath and a rigid shield structured so that the sheath cannot be removed from the shield during normal use of the product and preferably should not be capable of happening without the use of tools with the specific intent to dismantle and possibly destroy the needle shield assembly. To this end, means for holding the sheath within the shield are provided so that the sheath cannot be removed from the shield during normal use of the syringe assembly. The holding means may include a first inwardly projecting ledge in the shield positioned proximally of the annular flange 47. A second inwardly projecting ledge in the shield positioned distally of annular flange 47 is provided to hold the open proximal end of the sheath in its position at the open proximal end of the shield. In this preferred embodiment the first inwardly projecting ledge is in the form of annular inwardly projecting shoulder 57. The second inwardly projecting ledge in this embodiment is in the form of an annular inwardly projecting shoulder 58.

It should also be noted that the instant invention does not require special and different techniques with respect to the removal or replacement of the needle shield assembly because the sheath and the shield are assembled together at all times during assembly, operation and disposal of the syringe. Accordingly, savings are achieved with respect to time and elimination of special training and the reduced potential for needle sticks.

In this preferred embodiment the means for holding the sheath within the shield includes annular flange 47 on the sheath and annular inwardly projecting shoulder 57 of the shield. The sheath is prevented from leaving the open proximal end of the shield by contact of bottom surface 50 of the annular flange with annular inwardly projecting shoulder 57 of the shield. Shoulder 57 acts to prevent the sheath from coming out of or being intentionally removed from the shield. Because the instant invention also includes embodiments with a shield having an open distal end the means for holding the sheath within the shield may also include interaction between annular inwardly projecting shoulder 58 and top surface 49 of annular flange 47 of the resilient sheath. The interference between shoulder 58 and top surface 49 on the shield prevents the sheath from moving upwardly further into the shield and prevents its removal through the distal end of the shield if the distal end of the shield is open.

The interaction of shoulder 58 and top of the shield and top surface 49 of the annular flange of the sheath performs another important function in that it maintains the relative position of the sheath with respect to the shield during installation of the needle shield assembly onto the barrel and needle assembly. The interference of shoulder 58 and top surface 49 acts to help force the sheath over the tip portion of the barrel to form a preferably air tight interference fit between the resilient sheath and the rigid tip portion of the barrel as best illustrated in FIG. 4.

In embodiments of the present invention wherein the sheath is tightly contained within the shield the means for holding the sheath within the shield may be accomplished by providing a projection such as annularly inwardly projecting shoulder 57 interacting against bottom surface 50 alone without the need for shoulder 58 and top surface 49.

It is also preferred that the structure of the needle sheath and shield be such that manual disassembly or assembly of the components is extremely difficult without the use of tools or adhesives. In the preferred embodiment the shield is of two piece construction having a distal member 61 and a proximal member 62. Distal member 61 includes annular inwardly projecting shoulder 58 and proximal member 62 includes annular inwardly projecting shoulder 57. In manufacturing, the needle shield is assembled by placing the resilient sheath into distal member 61 and then installing proximal member 62 to trap the needle sheath within the shield to form a needle shield assembly. In this preferred embodiment the proximal member is mechanically connected to the distal member through an interference fit between the outside surface of the distal member and the inside surface of the proximal member. It will be apparent to one skilled in the art that there are numerous structures and methods to provide for the fixed attachment of proximal member 62 to distal member 61 such as adhesives, heat sealing, ultrasonic welding and the like, and that the structure described herein in this preferred embodiment is merely exemplary of these many possibilities.

Another advantage of the structure of the preferred embodiment is that if it were possible for a person to obtain the needle shield of the preferred embodiment without a sheath, and a separate needle sheath, it would be virtually impossible for this person to use these elements in the manner of prior art devices because if the sheath were placed on a syringe barrel and needle assembly, the shield could not be installed over the sheath because the shoulder 57 would prevent the shield from engaging the annular flange of the needle sheath. This same structure and features prevent the separation of the components of a properly assembled needle shield of the present invention. It can be seen that the shield and the sheath are structured so that the shield cannot be manually assembled or manually separated from the sheath while the sheath is properly positioned sealing the cannula and engaging the tip portion of the barrel.

Figure 6:
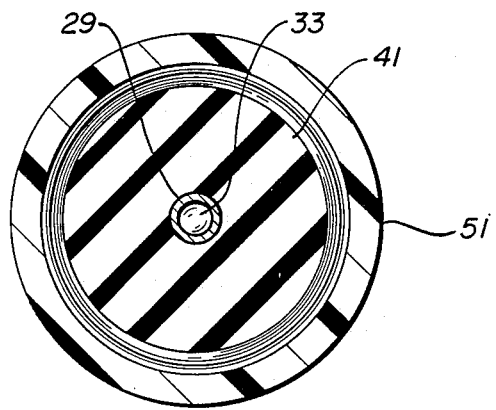
FIG. 6 is a cross sectional view of the syringe assembly of FIG. 4 taken along line 6—6.

The resilient sheath of the present invention also includes cannula sealing means at the distal end of receptacle 46 for providing a fluid-tight seal between lumen 33 and the environment of the syringe assembly. In this preferred embodiment the cannula sealing means includes an elongate retention conduit 65 having a sidewall 67 adapted to accept the distal end of cannula 29 in a fluid-tight engagement between the outside of the cannula and the conduit sidewall as best illustrated in FIGS. 3, 4 and 6. In this preferred embodiment the elongate retention conduit includes a circularly shaped cross section portion having a diameter less than the outside diameter of the cannula.

In this preferred embodiment a lubricant is provided on the cannula to reduce the forces required for the cannula to penetrate an injection vial or a patient's flesh. This lubricant may also enhance the assembly of the needle shield assembly to the syringe barrel and needle assembly by facilitating the engagement of the cannula 29 into elongate retention conduit 65.

Needle shield assembly 40 is positioned with distal end 31 of cannula 29 engaging cannula elongate retention conduit to seal the cannula lumen and proximal end 43 of the sheath removably engaging and sealing the interface between the sheath and the tip portion of the barrel so that the resilient sheath surrounds the entire portion of the cannula which extends outwardly from the tip portion. The sealing of the cannula contains the medicament within the syringe barrel and protects it from the environment, and the sealing of the area around the tip portion covers and protects the cleanliness of the exterior portions of the cannula and in the preferred embodiment is intended to protect the sterility of the cannula. It is an important feature of the instant invention that one continuous element, the resilient sheath, seals the cannula and the exterior of the tip portion to protect the cleanliness and sterility of the cannula. Multiple components to perform these functions may present problems with respect to leaking or providing an ineffective seal which may not protect cleanliness and/or sterility of the cannula.

The needle shield assembly is easily removed from the barrel and cannula using manual force applied to the shield. Using care it may be reassembled in the same fashion to protect persons coming in contact with the syringe assembly from accidental needle sticks.

In this embodiment rigid shield 51 includes aperture 68 at its distal end. The aperture is provided to facilitate sterilization by allowing sterilizing gases to access the interior of the needle shield assembly. An aperture may also provided to aid in the assembly of the needle sheath and distal portion 61 of the shield. If the outside diameter of the sheath approaches the inside diameter or shape of the rigid shield assembly of the parts may tend to trap air which can escape through aperture 68. It is also within the purview of the instant invention to provide multiple apertures at the distal end or in other portions of the rigid shield. It is also within the purview of the instant invention to provide a rigid shield having an aperture at the distal end which is substantially coincident with the inside diameter of the shield at the distal end so that the distal end is open.

After the needle shield assembly is removed, the remaining portion of the hypodermic syringe assembly may be used to inject medication into a patient using known safe techniques. If the needle shield assembly is installed onto the barrel and needle assembly after injection, the rigid shield of the preferred embodiment helps prevent accidental needle sticks by providing a shield structure without holes or gaps in the sidewall or at its open proximal end. These holes and gaps as seen in prior art shields can allow a needle to pass through the sheath and then out through the holes or gaps into the user's hand.

Referring now to FIGS. 8-10 wherein an alternative syringe assembly 70 is illustrated. In this alternative embodiment the structure of the syringe assembly is substantially similar to the syringe assembly of the embodiment of FIGS. 1-7. Accordingly, substantially similar components that perform substantially similar functions will be numbered identically to those components of the embodiment of FIGS. 1-7 except a suffix "a" will be used to identify those components in FIGS. 8-10.

In this alternative embodiment, syringe assembly 70 includes an elongate barrel 21a having an open proximal end (not shown), a chamber 23a for retaining fluid and a tip portion 25a extending from a distal end of the barrel having a passageway 28a therethrough communicating with said chamber. A needle cannula 29a having a distal end 31a including a sharpened point 32a extends outwardly from the tip portion and includes a lumen 33a in fluid communication with the passageway. A needle shield assembly 71 includes a resilient needle sheath 72 having an open proximal end 73, a closed distal end 74, a sidewall 75 defining a receptacle 76 therein. Resilient needle sheath 72 is positioned within an elongate rigid shield 51a having an open proximal end 52a, a distal end 53a and a sidewall 55a therebetween. Means for holding the sheath within the shield so that the sheath cannot be removed from the shield during normal use of the syringe is provided as described for the preferred embodiment of FIGS. 1-7.

Sheath 72 also includes cannula sealing means at distal end 74 of the receptacle 76. In this embodiment the length of the cannula projecting outwardly from the tip portion of the syringe barrel and/or the length of the receptacle in the resilient needle sheath are chosen so that when the needle shield assembly is properly positioned on tip portion 25a of the barrel the sharp point of the distal end of the cannula is embedded in distal end 74 of sheath 72 with portions of the sheath occluding lumen 33a, as best illustrated in FIGS. 9 and 10. It is not necessary in this embodiment to have a cannula retention conduit such as the embodiment of FIGS. 1-7 since the sealing of the cannula is accomplished by embedding the tip of the cannula in the distal end of the needle sheath.

The syringe barrel may be constructed of a wide variety of materials such as metals, plastics and ceramics. Glass is preferred due to its transparency, low moisture vapor transmission rate and compatibility with many medication formulations. The needle shield of the instant invention is especially desirable for glass syringes because the resilient needle sheath is more capable of engaging a glass syringe barrel tip which normally is subject to broader dimensional tolerances than metal or injection molded plastic barrel tip portions.

A wide variety of materials such as natural rubber, synthetic rubber, thermoplastic elastomers and thermoplastics are suitable for the shield with natural rubber being preferred. More rigid materials, such as thermoplastics, are more suitable for embodiments where a cannula tip is not embedded in the distal end of the needle shield because of the potential for the more rigid material to damage the sharp cannula point. A wide variety of materials, such as natural rubber, synthetic rubber and thermoplastic elastomers are suitable for the stopper with natural rubber and butyl rubber being preferred. A wide variety of medical grade lubricants are suitable for use in lubricating the needle cannula with medical grade silicone lubricants such as Dow Corning DC360, a dimethyl polysiloxane silicone lubricant. A wide variety of materials such as thermoplastics, thermosetting plastics and metals or combinations thereof are suitable for the shield. Injection moldable thermoplastics are preferred. It is preferred that the needle cannula be sterile at the time of use. Accordingly, materials should be chosen for compatibility with the sterilization process being used.

Thus, the present invention provides a straight forward, reliable, easily fabricated syringe having a needle shield assembly which retains the cannula sealing and cleanliness protecting features of the resilient needle sheath, and incorporates a rigid shield to help prevent accidental needle sticks during all phases of the assembly and operation and disposal of the syringe.

What is claimed is:

1. A hypodermic syringe assembly comprising:
   an elongate barrel having an open proximal end, a chamber for retaining fluid and a tip portion extending from a distal end of said barrel having a passageway therethrough communicating with said chamber;
   a needle cannula having a distal end extending outwardly from said tip portion including a lumen therethrough in fluid communication with said passageway;
   a needle shield assembly including a resilient needle sheath having an open proximal end, a closed distal end, a sidewall defining a receptacle therein, said resilient needle sheath being positioned within an elongate rigid needle shield having an open proximal end, a closed distal end and a sidewall therebetween;

means for holding said sheath within said shield so that said sheath cannot be removed from said shield during normal use of said syringe assembly, said sheath including cannula sealing means at said distal end of said receptacle for providing a fluid-tight seal between said lumen and the environment of said syringe assembly;

said needle shield assembly being positioned with said distal end of said cannula engaging said cannula sealing means and said proximal end of said sheath removably engaging said tip portion to hold said shield assembly on said barrel while simultaneously sealing said lumen of said cannula so that said sheath surrounds the entire portion of said cannula which extends outwardly from said tip portion;

said shield and said sheath being structured so that said shield cannot be manually assembled to or manually separated from said sheath while said sheath is properly positioned sealing said cannula and engaging said tip portion of said barrel; and said needle shield assembly being easily engageable to and removable from said barrel and said cannula using manual force applied to said shield.

2. The hypodermic syringe assembly of claim 1 wherein said cannula sealing means includes an elongate retention conduit having a sidewall adapted to accept said distal end of said cannula in fluid-tight engagement between the outside of said cannula and said conduit sidewall.

3. The hypodermic syringe assembly of claim 2 wherein said retention conduit includes a circularly shaped cross section portion having a diameter which is less than the outside diameter of said cannula.

4. The hypodermic syringe assembly of claim 1, wherein said sealing means includes said cannula being long enough so that when said needle shield assembly is positioned on said tip portion said distal end of said cannula is embedded in said closed distal end of said sheath with portions of said sheath occluding said lumen.

5. The hypodermic syringe assembly of claim 1 wherein said needle sheath includes a projection extending outwardly from its proximal end, and said means for holding said sheath within said shield including a first inwardly projecting ledge, in said shield, positioned proximally of said sheath projection.

6. The hypodermic syringe assembly of claim 5 wherein said holding means further includes a second inwardly projecting ledge, in said shield, positioned distally of said sheath projection.

7. The hypodermic syringe assembly of claim 5 wherein said sheath projection is an annular flange positioned at said proximal end of said sheath.

8. The hypodermic syringe assembly of claim 6 wherein said inwardly projecting ledges are annular inwardly projecting shoulders.

9. The hypodermic syringe assembly of claim 5 wherein said shield comprises a distal member including said first inwardly projecting ledge and a proximal member including said second inwardly projecting ledge, said proximal member and said distal member being joined together to form said shield.

10. The hypodermic syringe assembly of claim 1 wherein said shield includes an aperture in said distal end allowing fluid communication between portions of the exterior of said sheath and the environment of said syringe assembly.

11. The hypodermic syringe assembly of claim 1 further including a stopper slidably positioned in fluid-tight engagement inside said barrel adapted to engage a plunger rod to facilitate its operation, said stopper capable of moving fluid from said chamber through said passageway upon its movement toward said distal end, said stopper capable of facilitating the drawing of fluid into said chamber through said passageway upon its movement away from said distal end.

12. The hypodermic syringe assembly of claim 11 further including medicament within said chamber between said stopper and said distal end of said barrel.

13. The hypodermic syringe assembly of claim 11 further including a plunger rod engaged to said stopper and extending outwardly from said proximal end of said barrel.

14. The hypodermic syringe assembly of claim 1 wherein said sheath is made from material selected from the group consisting of natural rubber, synthetic rubber and thermoplastic elastomers.

15. The hypodermic syringe assembly of claim 1 wherein said shield is made of rigid material selected from the group consisting of thermoplastic, thermosetting plastic, metals and combinations thereof.

16. The hypodermic syringe assembly of claim 1 wherein said barrel is made of glass.

17. A hypodermic syringe assembly comprising a barrel having an open proximal end, a chamber for retaining fluid and a tip portion extending from a distal end of said barrel having a passageway therethrough communicating with said chamber;

a needle cannula having a distal end extending outwardly from said tip portion including a lumen therethrough in fluid communication with said passageway;

a needle shield assembly including a resilient needle sheath having an open proximal end, a closed distal end, a sidewall defining a receptacle therein, said resilient needle sheath being positioned within an elongate rigid needle shield having an open proximal end; a distal end and a sidewall therebetween;

means for holding said sheath within said shield so that said sheath cannot be removed from said shield during normal use of said syringe assembly, said sheath including cannula sealing means at said distal end of said receptacle;

said needle shield assembly being positioned with said distal end of said cannula engaging said cannula sealing means and said proximal end of said needle sheath removably engaging said tip portion to hold said shield assembly on said barrel while simultaneously sealing said lumen of said cannula so that said sheath surrounds the entire portion of said cannula which extends outwardly from said tip portion.

18. A hypodermic syringe assembly comprising an elongate barrel having an open proximal end, a chamber for retaining fluid and a tip portion extending from a distal end of said barrel having a passageway therethrough communicating with said chamber;

a needle cannula having a distal end extending outwardly from said tip portion including a lumen therethrough in fluid communication with said passageway;

a needle shield assembly including a resilient needle sheath having an open proximal end, a closed distal end, a sidewall defining a receptacle therein, a projection extending outwardly from said proximal end, said resilient needle sheath being positioned within an elongate rigid shield having an open proximal end, a distal end and a sidewall therebetween;

means for holding said sheath within said shield so that said sheath cannot be removed from said shield during normal use of said syringe assembly, said holding means including a first inwardly projecting ledge in said shield positioned proximally of said sheath projection;

said sheath including cannula sealing means at said distal end of said receptacle for providing a fluid-tight seal between said lumen and the environment of said syringe assembly including an elongate retention conduit having a sidewall adapted to accept said distal end of said cannula in fluid-tight engagement between the outside of said cannula and said conduit sidewall;

said needle shield assembly being positioned with said distal end of said cannula engaging said cannula sealing means and said proximal end of said sheath removably engaging said tip portion to hold said needle shield assembly on said barrel while simultaneously sealing said lumen of said cannula so that said sheath surrounds the entire portion of said cannula which extends outwardly from said tip portion, said shield and said sheath being structured so that said shield cannot be manually assembled to or manually separated from said sheath while said sheath is properly positioned sealing said cannula and engaging said tip portion of said barrel;

said needle shield assembly being easily engageable to and removable from said barrel and said cannula using manual force applied to said shield;

a stopper slidably positioned in fluid-tight engagement inside said barrel adapted to engage a plunger rod to facilitate its operation, said stopper capable of moving fluid from said chamber through said passageway upon its movement toward said distal end, said stopper capable of facilitating the drawing of fluid into said chamber through said passageway upon its movement away from said distal end; and medicament within said chamber between said stopper and said distal end of said barrel.

19. The hypodermic syringe assembly of claim 18 wherein said holding means further includes a second inwardly projecting ledge in said shield positioned distally of said sheath projection.

20. The hypodermic syringe assembly of claim 18 wherein said sheath projection is an annular flange positioned at said proximal end of said sheath and said first inwardly projecting ledge is an annular inwardly projecting shoulder.

21. A needle shield assembly for use with a syringe barrel having a chamber for retaining fluid, a tip portion extending outwardly from a distal end of said barrel having a passageway therethrough and a needle having a distal end extending outwardly from said tip portion having a lumen therethrough in fluid communication with said passageway comprising:

a resilient needle sheath having an open proximal end, a closed distal end, a sidewall defining a receptacle therein, and a projection extending outwardly from said proximal end;

said resilient needle sheath being positioned within an elongate rigid shield having an open proximal end, a closed distal end and a sidewall therebetween;

means for holding said sheath within said shield so that said sheath cannot be removed from said shield during normal use of said syringe assembly including a first inwardly projecting ledge in said shield, positioned proximally of said sheath projection;

said sheath including cannula sealing means at said distal end of said receptacle for providing a fluid-tight seal between said lumen and the environment of said syringe assembly;

said needle shield assembly being sized so that said distal end of said cannula sealing means is adapted to engage said cannula and said proximal end of said sheath is adapted to removably engage said tip portion to hold said shield assembly on said barrel while simultaneously sealing said lumen of said cannula so that said sheath may surround the entire portion of said cannula which extends outwardly from said tip portion;

said shield and said sheath being structured so that said shield cannot be manually assembled to or manually separated from said sheath while said sheath is properly positioned sealing said cannula and engaging said tip portion of said barrel; and said needle shield assembly being easily engageable to and removable from said barrel and said cannula using manual force.

22. The needle shield assembly of claim 21 wherein said cannula sealing means includes an elongate retention conduit having a sidewall adapted to accept said distal end of said cannula in fluid-tight engagement between the outside of said cannula and said conduit sidewall.

23. The needle shield assembly of claim 21 wherein said holding means further includes a second inwardly projecting ledge in said shield positioned distally of said sheath projection.

24. The needle shield assembly of claim 21 wherein said sheath projection is an annular flange positioned at said proximal end of said sheath and said first inwardly projecting ledge is an annular inwardly directed shoulder.

25. The needle shield assembly of claim 23 wherein said shield comprises a proximal member including said first inwardly projecting ledge and a distal member including said second inwardly projecting ledge, said proximal member and said distal member being joined together to form said shield.

26. The needle shield assembly of claim 21 wherein said shield includes an aperture in said distal end allowing fluid communication between portions of the exterior of said sheath and the environment of said syringe assembly.

27. The needle shield assembly of claim 21 wherein said sheath is made of natural rubber.

* * * * *